(12) United States Patent
Koehler et al.

(10) Patent No.: US 7,169,947 B2
(45) Date of Patent: Jan. 30, 2007

(54) DICOPPER(I) OXALATE COMPLEXES FOR USE AS PRECURSOR SUBSTANCES IN METALLIC COPPER DEPOSITION

(75) Inventors: Katrin Koehler, Goettingen (DE); Franc Meyer, Goettingen (DE)

(73) Assignee: Basf Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/519,163

(22) PCT Filed: Jun. 5, 2003

(86) PCT No.: PCT/EP03/05897

§ 371 (c)(1),
(2), (4) Date: Dec. 23, 2004

(87) PCT Pub. No.: WO04/000850

PCT Pub. Date: Dec. 31, 2003

(65) Prior Publication Data

US 2005/0226997 A1    Oct. 13, 2005

(30) Foreign Application Priority Data

Jun. 24, 2002 (DE) ................................ 102 28 050

(51) Int. Cl.
*C07F 1/08* (2006.01)
*C23C 16/00* (2006.01)

(52) U.S. Cl. .................... 556/113; 556/12; 556/13; 556/21; 556/112; 546/2; 427/124; 427/250

(58) Field of Classification Search .................. 556/12, 556/13, 21, 112, 113; 427/250, 124; 546/2
See application file for complete search history.

(56) References Cited

U.S. PATENT DOCUMENTS

| 4,387,055 A | 6/1983 | Doyle |
| 5,441,766 A * | 8/1995 | Choi et al. .................. 427/250 |

FOREIGN PATENT DOCUMENTS

WO    WO 0063461    10/2000

OTHER PUBLICATIONS

Database CA Online! Chemical Abstracts Service, Columbus, Ohio, US; Diez, Josefina et al:"Preparation of New Mono and Polynuclear Bis (Triphenylphosphine) Copper (I) Derivatives Containing Mono and Bidentate N-Heterocycles, 8-Hyroxyquinoline and Oxalate Ligands" Retrieved From STN Database Accession No. 108:178938 (1988).

* cited by examiner

*Primary Examiner*—Porfirio Nazario-Gonzalez
(74) *Attorney, Agent, or Firm*—Millen, White, Zelano, Branigan, P.C.

(57) ABSTRACT

The invention relates to dicopper(I) oxalate complexes stabilised by neutral Lewis base components and to the use thereof as precursors for the deposition of metallic copper. The neutral Lewis bases used are alkynes or alkenes containing at least one silyl or ester group, or nitriles, saturated or unsaturated nitrogen ligands, phosphites, trialkyl-phosphines or oxygen- or sulfur-containing ligands.

24 Claims, 2 Drawing Sheets

DICOPPER(I) OXALATE COMPLEXES FOR USE AS PRECURSOR SUBSTANCES IN METALLIC COPPER DEPOSITION

The invention relates to dicopper(I) oxalate complexes stabilised by neutral Lewis base components and to the use thereof as precursors for the deposition of metallic copper. The neutral Lewis bases used are alkynes or alkenes containing at least one silyl or ester group, or nitriles, saturated or unsaturated nitrogen ligands, phosphites, trialkyl-phosphines or oxygen- or sulfur-containing ligands.

1. PRIOR ART AND OBJECT OF THE INVENTION

For the deposition of thin copper films on substrates, many organo-copper precursors have now been disclosed. Copper compounds in the oxidation state +1 containing a β-diketonate ligand and a neutral Lewis base L, such as, for example, an alkene or alkyne, have proven to be highly promising substances. Complexes of this type and the use thereof as precursors in the CVD (chemical vapour deposition) process are described, for example, in U.S. Pat. No. 5,220,044, WO 00/71550, WO 00/17278, U.S. Pat. No. 6,130,345 or Chem. Mater. 2001, 13, 3993; Inorg. Chem. 2001, 40, 6167; Chem. Mater. 1992, 4, 365; Organometallics 2001, 20, 4001. Preference is given to the use of fluorine-containing β-diketonate ligands, such as, for example, hexafluoroacetylacetonate, since the corresponding copper (I) complexes have much higher thermal stability and higher volatility than their fluorine-free analogues. Fluorine-free copper(I) β-diketonate complexes, such as, for example, alkyne-stabilised copper(I) acetylacetonates, are extremely oxygen-sensitive, decompose even at 0° C. (Chem. Ber. 1995, 128, 525) and are thus no longer suitable as precursors for the CVD process. The deposition of the copper layer takes place in a thermally induced disproportionation in accordance with the following equation:

2 $LCu^{I}$(β-diketonate)→$Cu^{0}$+$Cu^{II}$(β-diketonate)$_2$+2 L

The resultant $Cu^{II}$(β-diketonate)$_2$ and Lewis base L are volatile under the conditions used in the CVD process and can thus be removed from the system. Ideally, a highly pure copper film remains. However, only 50% of the copper(I) precursor employed can be converted into copper(0) in this reaction, the remaining 50% ending in the corresponding $Cu^{II}$(β-diketonate)$_2$. The same result is obtained on use of β-keto esters instead of β-diketones, as described, for example, in WO 00/08225 or U.S. Pat. No. 5,441,766. However, it has proven disadvantageous on use of fluorine-containing copper(I) precursors that the adhesion of the copper films to various substrate surfaces is not perfect, which can probably be attributed to the van der Waals forces of the fluorine atoms in the precursor molecule and thus to repulsive interactions. In addition, there is a risk of contamination of the wafer in microelectronics, especially of the silicon with fluorine, which results in the wafer being unusable.

Complete conversion to copper is achieved using Lewis base-stabilised copper(I) alkoxides of the formula $LCu^{I}OR$ (EP 0468396) and Lewis base-stabilised cyclopentadienyl-copper(I) compounds of the formula $LCu^{I}(\eta^5\text{-}C_5R_5)$, described in EP 0297348 and DE 4124686. Some of the examples in the said patents are even fluorine-free and stable at 25° C. However, since the thermal decomposition reactions do not proceed in a defined manner in these cases, free-radical species are formed in the decomposition reactions, unfortunately resulting in contaminated copper films (oxygen about 5%, carbon about 1%) (MRS Bulletin/August 1994, 41; Chem. Mater. 1992, 4, 577).

The object of the present invention was therefore to provide fluorine-free copper(I) precursors for the deposition of metallic copper which are simple and inexpensive to prepare, are stable thermally and if possible to air and can be converted completely into metallic copper films by thermal methods in a defined decomposition reaction in the temperature range from about 50 to 400° C. with formation of defined molecular, copper-free, nontoxic and if possible gaseous by-products. Further objects of the present invention are, in addition to a process for the preparation of the precursor substances according to the invention which can be carried out simply and inexpensively, also to provide a suitable process for the preparation of thin, highly pure copper films or layers with the aid of these precursors and thus also improved highly pure, thin copper layers.

The object is achieved by compounds of the general formula (I)

in which copper is in the oxidation state +1, and

L is R—C≡C—R' having at least one silyl or ester group, R'HC=CHR having at least one silyl or ester group, $R'_3Si$—C≡C—R', $R'_3N$, $R'_2N(CH_2)_nNR'_2$, substituted or unsubstituted 2,2'-bipyridine, 1,10-phenanthroline, $P(OR')_3$, $P(alkyl)_3$, R'—O—R', R'—O($CH_2$)$_n$O—R', R'—S—R', R'—S($CH_2$)$_n$S—R' or a nitrile from the group consisting of $CH_3$—C≡N, $^tBu$—C≡N, $C_4H_9$C≡N and Ph—C≡N, where R is A, aryl, alkylaryl or alkynyl having at least one $SiR'_3$ or COOR' group, and R' is R, H, A, aryl, alkylaryl or alkynyl, where L, R and R' may each, independently of one another, adopt identical or different meanings in different positions of the molecule, A is straight-chain or branched C1–C30-alkyl, C3–C30-cycloalkyl, straight-chain or branched C2–C30-alkenyl or straight-chain or branched C3–C30-cycloalkenyl, aryl is C6–C10-aryl or alkylaryl, alkylaryl is C7–C18-alkylaryl, alkynyl is straight-chain or branched C2–C30-alkynyl.

Compounds according to the invention are therefore also compounds of the general formula (I) in which A is straight-chain or branched C1–C9-alkyl, straight-chain or branched C3–C9-cycloalkyl, straight-chain or branched C2–C9-alkenyl or straight-chain or branched C3–C9-cyclo-alkenyl, aryl is phenyl or naphthyl, alkylaryl is tolyl or mesityl, alkynyl is straight-chain or branched C2–C9-alkynyl, and L, R and R' may each, independently of one another, adopt identical or different meanings in different positions of the molecule.

Sub-groups are formed by compounds of the general formula (I) in which

I.

A is straight-chain or branched C1–C4-alkyl from the group consisting of methyl, ethyl, n- and i-propyl and n-, i- and tert-butyl, C3–C6-cycloalkyl from the group consisting of cyclopropyl, cyclobutyl, cyclopentyl and cyclohexyl, straight-chain or branched C2–C6-alkenyl from the group consisting of vinyl, propenyl, butenyl, pentenyl and hexenyl, or C3–C6-cycloalkenyl from the group consisting of cyclopropenyl, cyclobutenyl, cyclopentenyl, cyclopentadienyl and methylcyclopentadienyl, aryl is phenyl or naphthyl, alkylaryl is tolyl or mesityl, alkynyl is straight-chain or branched C2–C6-alkynyl from the group consisting of ethynyl, propynyl, butynyl, pentynyl and hexynyl, and R and R' may each, independently of one another, adopt identical or different meanings in different positions of the molecule, or

II.

L is R—C≡C—R' or R'HC=CHR, each having at least one silyl or ester group, and the radicals R and R' are as defined in claim 1, or

III.

L is R'$_3$Si—C≡C—R', where

R' is SiMe$_3$, CH$_3$, C$_2$H$_5$, C$_3$H$_7$, C$_4$H$_9$, phenyl, COOMe or COOEt, or

IV.

L is an alkyne selected from the group consisting of Me$_3$Si—C≡C—SiMe$_3$, Me$_3$Si—C≡C—"Bu, MeOOC—C≡C—COOMe, EtOOC—C≡C—COOEt and Me$_3$Si—C≡C—R', in which R' is CH$_3$, C$_2$H$_5$, C$_3$H$_7$, phenyl, COOMe or COOEt, or

V.

L is an alkene selected from the group consisting of H$_2$C=CHSiMe$_3$, H$_2$C=CHCOOCH$_3$, H$_2$C=CHCOOC$_2$H$_5$ and H$_2$C=CHSiR'$_3$, in which R', independently of one another, is CH$_3$, C$_2$H$_5$, C$_3$H$_7$, C$_4$H$_9$, HC=CH$_2$ or phenyl, or

VI.

L is a compound selected from the group consisting of CH$_3$—C≡N, 'Bu C≡N, C$_4$H$_9$C≡N, Ph—C≡N; N(CH$_3$)$_3$, N(C$_2$H$_5$)$_3$, H$_2$N—(CH$_2$)$_2$—NH$_2$, (CH$_3$)$_2$N—(CH$_2$)$_2$—N(CH$_3$)$_2$, (C$_2$H$_5$)$_2$N—(CH$_2$)$_2$—N(C$_2$H$_5$)$_2$, H$_2$N—(CH$_2$)$_4$—NH$_2$, (CH$_3$)$_2$N—(CH$_2$)$_4$—N(CH$_3$)$_2$, (C$_2$H$_5$)$_2$N—(CH$_2$)$_4$—N(C$_2$H$_5$)$_2$, 2,9-dimethyl-1,10phenanthroline; P(OCH$_3$)$_3$, P(OC$_2$H$_5$)$_3$, P(OC$_6$H$_{11}$)$_3$, P(OPh)$_3$; P(CH$_3$)$_3$, P(C$_2$H$_5$)$_3$, P(C$_3$H$_7$)$_3$, P(C$_4$H$_9$)$_3$, P(C$_6$H$_{11}$)$_3$; C$_2$H$_5$—O—C$_2$H$_5$, CH$_3$—O—C$_4$H$_9$, CH$_3$O—(CH$_2$)$_2$—OCH$_3$, C$_2$H$_5$O—(CH$_2$)$_2$—OC$_2$H$_5$, CH$_3$—S—CH$_3$, C$_2$H$_5$—S—C$_2$H$_5$, C$_3$H$_7$—S—C$_3$H$_7$, Ph—S—Ph, CH$_3$S—(CH$_2$)$_2$—SCH$_3$, CH$_3$S—(CH$_2$)$_3$—SCH$_3$, C$_2$H$_5$S—(CH$_2$)$_2$—SC$_2$H$_5$ and PhS—(CH$_2$)$_2$—SPh.

In particular, the object of the present invention is achieved by the novel compounds of the general formula (I):
di{[bis(trimethylsilyl)acetylene]copper(I)}oxalate,
di{[(trimethylsilyl)(n-butyl)acetylene]copper(I)}oxalate,
di[(vinyl-t-butyldimethylsilyl)copper(I)]oxalate and
di[(vinyldiethylmethylsilane)copper(I)]oxalate.

The object of the present invention is also achieved by a process for the preparation of the compounds of the general formula (I) as indicated by reacting Cu$_2$O with oxalic acid and a Lewis base L in an inert solvent, and isolating the resultant product. In particular, the object is achieved by the particular embodiments of the process as claimed in claims 11 to 21.

In accordance with the invention, the compounds of the general formula (I) according to claims 1 to 9 are used for the production of highly pure, thin metallic copper layers.

Highly pure, thin metallic copper layers are produced by a process in which compounds of the general formula (I) are heated, causing elimination of the Lewis base L and deposition of metallic copper through decarboxylation.

The elimination of the Lewis base L is carried out at a temperature in the range from about 50 to about 200° C. The decarboxylation with formation of metallic copper and carbon dioxide which takes place as the second reaction is completed at a temperature in the range from about 150 to 350° C.

The Lewis base L eliminated is recycled and re-employed in a process for the preparation of the compounds of the general formula (I) and used for the production of highly pure, thin metallic copper layers.

The object according to the invention is thus achieved, in particular, by highly pure, thin metallic copper layers having improved properties produced using a compound of the general formula (I) in the process according to the invention.

2. DESCRIPTION OF THE INVENTION

The present invention provides compounds of the general formula (I)

(I)

in each of which, independently of the position in the complex and of one another,

L is an alkyne R—C≡C—R' or alkene R'HC═CHR which contains at least one silyl or ester group. L may furthermore be a nitrile R'—C≡N, a saturated or unsaturated nitrogen ligand, a phosphite P(OR')$_3$, a trialkylphosphine P(alkyl)$_3$, an ether R'—O—R', a diether, a thioether R'—S—R' or a dithioether. The oxidation state of the copper is +1.

R can be alkyl, cycloalkyl, alkenyl, cycloalkenyl, aryl, alkylaryl or alkynyl having at least one SiR'$_3$ or COOR' group.

R' can, independently of one another, be R or H, alkyl, cycloalkyl, alkenyl, cycloalkenyl, aryl, alkylaryl or alkynyl.

The compounds of the general formula (I) are prepared by reaction of Cu$_2$O, oxalic acid and the neutral ligand L or the two different neutral ligands in an inert aprotic organic solvent. The compounds of the general formula (I) can be isolated in the pure form as temperature-stable substances. In addition, the substances obtained are distinguished by surprisingly and unusually high oxidation stability; they can be handled in air without problems, which enormously simplifies subsequent use of the substances as precursors for the deposition of metallic copper.

If the compounds of the general formula (I) are heated, a highly pure copper mirror remains; all by-products are volatile and can thus be removed from the reaction site very simply. The thermal decomposition proceeds in accordance with the following equation:

The only reaction products formed, besides metallic copper, are carbon dioxide and the Lewis base L, which can be regenerated and re-used.

The compounds of the general formula (I) can be used as precursors for the deposition of metallic copper. The deposition can be carried out from the gas phase or from a solution of precursor and a suitable solvent or from the solid state of the precursor through contact of the precursor with a heated substrate. It is advantageous compared with the prior art that copper(I) precursors with which metallic copper can be deposited to the extent of 100% in a defined free-radical-free decomposition reaction with formation of highly pure copper films are accessible for the first time. The yield of deposited metallic copper can thus be increased from 50 to 100% compared with the prior art. The high stability and insensitivity of the compounds, in particular the high oxidation stability, enormously simplify handling of the compounds in the process for the deposition of metallic copper and thus have a favourable effect on the deposition process in terms of cost.

The advantages of the compounds of the general formula (I) compared with the substance used in the prior art (CupraSelect®) are thus: better physical properties, such as higher thermal stability, better chemical properties, such as higher oxidation stability, simpler handling, less expensive synthesis owing to the much cheaper starting material oxalic acid compared with hexafluoroacetylacetone, double the yield of metallic copper in the deposition process, copper-free and nontoxic by-products, fewer by-products and thus less environmental pollution. In addition, the compounds contain no fluorine atoms which can result in fluorine contamination and thus in the wafers being unusable.

Overall, the synthesis of the copper(I) precursors according to the invention is thus simpler and less expensive than that of the commercially available copper(I) precursor CupraSelect®, which is (trimethyl-vinylsilane)copper(I) hexafluoroacetylacetonate. At the same time, the precursors according to the invention enable both the quality of the copper coatings to be increased and the environmental friendliness of the process to be increased.

3. DETAILED DESCRIPTION OF THE INVENTION

Compounds of the general formula (I) according to the invention contain an oxalate dianion and two copper centres in the oxidation state +1, where the oxalate dianion is bonded as a bridge in a μ-1,2,3,4 mode to the two copper(I) centres. The dicopper(I) oxalate unit CuO$_2$C$_2$O$_2$Cu is stabilised by coordination of neutral ligands L to one copper(I) centre each, preferably two identical ligands L, so that the two copper(I) centres have an at least pseudo-trigonal-planar, if desired also a tetrahedral environment. The copper atoms present in the complex may be bonded to two different ligands L. For simplification, reference is generally made below to the ligand or Lewis base L, although this may also be taken to mean two different ligands or Lewis bases L.

L is an alkyne R—C≡C—R' or alkene R'HC═CHR which contains at least one silyl or ester group. L may furthermore be a nitrile R'—C≡N, a saturated or unsaturated nitrogen ligand, such as, for example, R'$_3$N, R'$_2$N(CH$_2$)$_n$NR'$_2$, substituted or unsubstituted 2,2'-bipyridine or 1,10-phenanthroline, a phosphite P(OR')$_3$, an alkylphosphine P(alkyl)$_3$, an ether R'—O—R', a diether, a thioether R'—S—R' or a dithioether. R in turn can be alkyl, cycloalkyl, alkenyl, cycloalkenyl, aryl, alkylaryl or alkynyl having at least one SiR'$_3$ or COOR' group. R' can be, independently of one another, R or H, alkyl, cycloalkyl, alkenyl, cycloalkenyl, aryl, alkylaryl or alkynyl.

Alkyl groups can be straight-chain or branched C1–C30-alkyl, preferably straight-chain or branched C1–C9-alkyl, particularly preferably straight-chain or branched C1–C4-alkyl from the group consisting of methyl, ethyl, n- and i-propyl and n-, i- and tert-butyl. Cycloalkyl groups can be straight-chain or branched C3–C30-cycloalkyl, preferably C3–C9-cycloalkyl, particularly preferably C3–C6-cycloalkyl from the group consisting of cyclopropyl, cyclobutyl, cyclopentyl and cyclohexyl.

Alkenyl groups can be straight-chain or branched C2–C30-alkenyl, preferably straight-chain or branched C2–C9-alkenyl, particularly preferably straight-chain or branched C2–C6-alkenyl from the group consisting of vinyl, propenyl, butenyl, pentenyl and hexenyl. Cycloalkenyl groups can be straight-chain or branched C3–C30-cycloalkenyl, preferably C3–C9-cycloalkenyl, particularly preferably C3–C6-cycloalkenyl from the group consisting of cyclopropenyl, cyclobutenyl, cyclopentenyl, cyclopentadienyl and methylcyclopentadienyl.

Aryl groups can be C6–C10-aryl, preferably phenyl or naphthyl. Alkylaryl can be C7–C18-alkylaryl, preferably tolyl or mesityl.

Alkynyl groups can be straight-chain or branched C2–C30-alkynyl, preferably straight-chain or branched C2–C9-alkynyl, particularly preferably straight-chain or branched C2–C6-alkynyl from the group consisting of ethynyl, propynyl, butynyl, pentynyl and hexynyl.

Particularly suitable neutral Lewis bases are alkynes of the formula R—C≡C—R' and alkenes of the formula R'HC=CHR which contain at least one silyl or ester group. Preference is given to the use of alkynes from the R'$_3$Si—C≡C—R' group, and particularly good results are obtained with the alkynes Me$_3$Si—C≡C—R' (R'=SiMe$_3$, CH$_3$, C$_2$H$_5$, C$_3$H$_7$, C$_4$H$_9$, phenyl, COOMe, COOEt) and with the alkynes MeOOC—C≡C—COOMe and EtOOC—C≡C—COOEt. Preference is given to the use of alkenes from the R'HC=CHR group, and particularly good properties are obtained with the alkenes H$_2$C=CHSiMe$_3$, H$_2$C=CHSiR'$_3$, in which R', independently of one another, can be CH$_3$, C$_2$H$_5$, C$_3$H$_7$, C$_4$H$_9$, HC=CH$_2$ or phenyl, and with the alkenes H$_2$C=CHCOOCH$_3$ and H$_2$C=CHCOOC$_2$H$_5$. Particularly good results are obtained with the alkynes Me$_3$Si—C≡C—SiMe$_3$, Me$_3$Si—C≡C—$^n$Bu and the alkenes H$_2$C=CHSiEt$_2$Me, H$_2$C=CHSiMe$_2$$^t$Bu.

The following are also suitable as neutral Lewis bases: nitriles R'C≡N, for example CH$_3$—C≡N, $^t$Bu C≡N, C$_4$H$_9$C≡N or Ph—C≡N; saturated or unsaturated nitrogen ligands R'$_3$N, such as, for example, N(CH$_3$)$_3$, N(C$_2$H$_5$)$_3$ or R'$_2$N(CH$_2$)$_n$NR'$_2$, such as, for example, H$_2$N—(CH$_2$)$_2$—NH$_2$, (CH$_3$)$_2$N—(CH$_2$)$_2$—N(CH$_3$)$_2$, (C$_2$H$_5$)$_2$N—(CH$_2$)$_2$—N(C$_2$H$_5$)$_2$, H$_2$N—(CH$_2$)$_4$—NH$_2$, (CH$_3$)$_2$N—(CH$_2$)$_4$—N(CH$_3$)$_2$, (C$_2$H$_5$)$_2$N—(CH$_2$)$_4$—N(C$_2$H$_5$)$_2$ or substituted or unsubstituted 2,2'-bipyridine or 1,10-phenanthroline or 2,9-dimethyl-1,10-phenanthroline; phosphites of the formula P(OR')$_3$, for example P(OCH$_3$)$_3$, P(OC$_2$H$_5$)$_3$, P(OC$_6$H$_{11}$)$_3$ or P(OPh)$_3$; trialkylphosphines of the formula PR'$_3$, for example P(CH$_3$)$_3$, P(C$_2$H$_5$)$_3$, P(C$_3$H$_7$)$_3$, P(C$_4$H$_9$)$_3$ or P(C$_6$H$_{11}$)$_3$; ethers of the formulae R'—O—R' and R'O—(CR'$_2$)$_n$—OR', for example C$_2$H$_5$—O—C$_2$H$_5$, CH$_3$—O—C$_4$H$_9$, CH$_3$O—(CH$_2$)$_2$—OCH$_3$ or C$_2$H$_5$O—(CH$_2$)$_2$—OC$_2$H$_5$; thioethers of the formulae R'—S—R' and R'S—(CR'$_2$)$_n$—SR', for example CH$_3$—S—CH$_3$, C$_2$H$_5$—S—C$_2$H$_5$, C$_3$H$_7$—S—C$_3$H$_7$, Ph—S—Ph, Ch$_3$S—(CH$_2$)$_2$—SCH$_3$, CH$_3$S—(CH$_2$)$_3$—SCH$_3$, C$_2$H$_5$S—(CH$_2$)$_2$—SC$_2$H$_5$ or PhS—(CH$_2$)$_2$—SPh.

The compounds of the general formula (I) are prepared by reaction of Cu$_2$O, oxalic acid and the Lewis base L under a protective-gas atmosphere in an inert aprotic organic solvent. The Lewis base L employed for this purpose can be two different Lewis bases L in an equimolar ratio. The sequence of addition of the components can be selected as desired. If the Lewis base L to be employed is a mixture of two corresponding compounds, the two compounds are preferably added to the reaction mixture simultaneously or mixed with one another before the addition. The starting compounds can be pre-dissolved or suspended in a suitable solvent or added without solvent as a solid or liquid. Suitable solvents which can be used for carrying out the reaction are inert aprotic solvents, such as open-chain or cyclic aliphatic and aromatic hydrocarbons, which may be partially halogenated, or ethers and cyclic ethers. Particular preference is given to the use of pentane, hexane, heptane, cyclohexane, toluene, methylene chloride, trichloro-methane, chlorobenzene, diethyl ether or tetrahydrofuran. The protective-gas atmosphere used can be nitrogen or argon. The stoichiometric ratio of the starting materials Cu$_2$O, oxalic acid and the Lewis base L is between 1:1:2 and 1:1:4, preferably between 1:1:2 and 1:1:3 and particularly preferably 1:1:2. The Lewis base L should not be added in a sub-stoichiometric amount with respect to oxalic acid and Cu$_2$O. The reaction can be carried out at a temperature in the range from −30 to +100° C., preferably from 0 to 50° C. and very preferably between 20 and 40° C. The highest yields are obtained at room temperature. The reaction time is between 1 and 24 hours, preferably between 2 and 8 hours and very preferably between 3 and 6 hours. The reaction solution changes beginning from a red suspension to a colourless or brownish solution or suspension, depending on the type of complex formed. The insoluble constituents are separated off. This can be carried out by filtration, centrifugation or other methods known to the person skilled in the art. A clear colourless, yellow or red solution is obtained, depending on the type of Lewis base L employed. The compounds of the general formula (I) are subsequently isolated. This can be carried out after the removal of the solvent by methods known to the person skilled in the art. If necessary, further purification is carried out. Instead of mechanical separation of the solids from the reaction mixture by filtration or other methods, it is also possible to carry out an extraction in order to remove the product formed. The compounds of the general formula (I) are, as already described above, surprisingly temperature-stable and can therefore be isolated well as pure substances and subsequently characterised analytically and spectroscopically.

The thermal behaviour of the compounds can be investigated by means of TGA (thermogravimetric analysis) and DSC (differential scanning calorimetry). Investigations carried out have shown that the decomposition of the compounds according to the invention takes place in 2 main steps:

Firstly, the Lewis base L is eliminated from the copper(I) complex. This elimination can also take place stepwise, depending on the compound, and can be detected by TGA. In the second step, decarboxylation takes place with formation of metallic copper and carbon dioxide through an internal redox reaction of the remaining fragment CuO$_2$C$_2$O$_2$Cu. The first step is carried out, depending on the precursor, at a temperature in the range from about 50 to about 200° C., and the second from about 150° C. and is complete at about 350° C. However, it is entirely possible for the elimination of the Lewis bases and the decarboxylation reaction to proceed in parallel on transition to higher temperatures. The residual content corresponds precisely to the copper content in the corresponding copper(I) precursor, so that the yield of metallic copper is 100% with the compounds of the general formula (I) and is thus double that of the prior art.

This efficient decomposition reaction results in fewer by-products with the compounds of the general formula (I) compared with the prior art. The free Lewis base L re-forms in the deposition process and can be collected by appropriate devices, such as, for example, cold traps in the exhaust air, and re-used; the second by-product formed in carbon dioxide. Compared with the prior art, in which copper(II) hexafluoroacetylacetonate and the Lewis base trimethylvinylsilane are formed as by-products, the by-products are copper-free, nontoxic and thus safer. The environmental pollution is thus significantly less than on use of the compounds of the prior art.

(Me$_3$Si—C≡C—SiMe$_3$)$_2$Cu$_2$O$_4$C$_2$ has proven to be a thermally stable compound which is extremely insensitive to oxidation. The compound is stable up to 100° C. and can be handled in air over a period of weeks. This is an enormous advance compared with the prior art since CupraSelect® decomposes slowly even from about 50° C. and the compound is also rapidly oxidised in air to give copper(II). This enables very much simpler handling not only in the synthesis, but also in the deposition process.

The compounds of the general formula (I) can be used as precursors for the deposition of metallic copper. The deposition of metallic copper films can take place from the gas phase or from a solution of precursor and a suitable solvent or from the solid state of the precursor through contact of the precursor with a heated substrate.

For illustration and for better understanding of the present invention, examples are given below. However, owing to the general validity of the inventive principle described, these are not suitable for reducing the scope of protection of the present application to just these examples. Furthermore, the contents of the cited patent applications are to be regarded as part of the disclosure content of the present invention which forms the basis of the description.

4. EXAMPLES

Example 1

Di{[bis(trimethylsilyl)acetylene]copper(I)}oxalate 8 g of $Me_3SiC \equiv CSiMe_3$ and 2.14 g of oxalic acid are added to a suspension of 3.4 g of $Cu_2O$ in 30 ml of methylene chloride under an inert-gas atmosphere, and the mixture is stirred at room temperature for 4 hours. In order to remove insoluble residues, the solution is passed through a frit with silica gel, and the residue is washed twice with methylene chloride on the frit. The colourless solution is evaporated, and colourless crystals of $(Me_3SiC \equiv CSiMe_3)_2 Cu_2O_4C_2$ are obtained at −30° C.

$C_{18}H_{36}Cu_2O_4Si_4$ (555.92 g/mol). Analysis [%]: calculated: C 38.9, H 6.5, found: C 38.7, H 6.6. IR (KBr) [cm$^{-1}$]: $v_{C \equiv C}$ 1935, $v_{CO2}$ 1642, 1354, 1309. $^1$H-NMR (CDCl$_3$) [ppm]: 0.30 (s, 36H, SiMe$_3$). $^{13}$C-NMR (CDCl$_3$) [ppm]: 0.0 (SiMe$_3$), 114.2 (C≡C), 171.8 (CO$_2$). MS (m/e (%)): 788 (25) [M+Cu(Me$_3$SiC≡CSiMe$_3$)]$^+$, 618 (10) [M+Cu]$^+$, 403 (68) [M−CuO$_4$C$_2$]$^+$, 233 (100) [M−(Me$_3$SiC≡CSiMe$_3$)CuO$_4$C$_2$]$^+$. TG (30–1000° C., 5° C./min) two-step decomposition, 1st step temperature range 100–170° C., weight drop 65% (2 Me$_3$SiC≡CSiMe$_3$), 2nd step temperature range 230–290° C., weight drop 11% (2 CO$_2$), residual content 24% (2 Cu).

Figure 1:
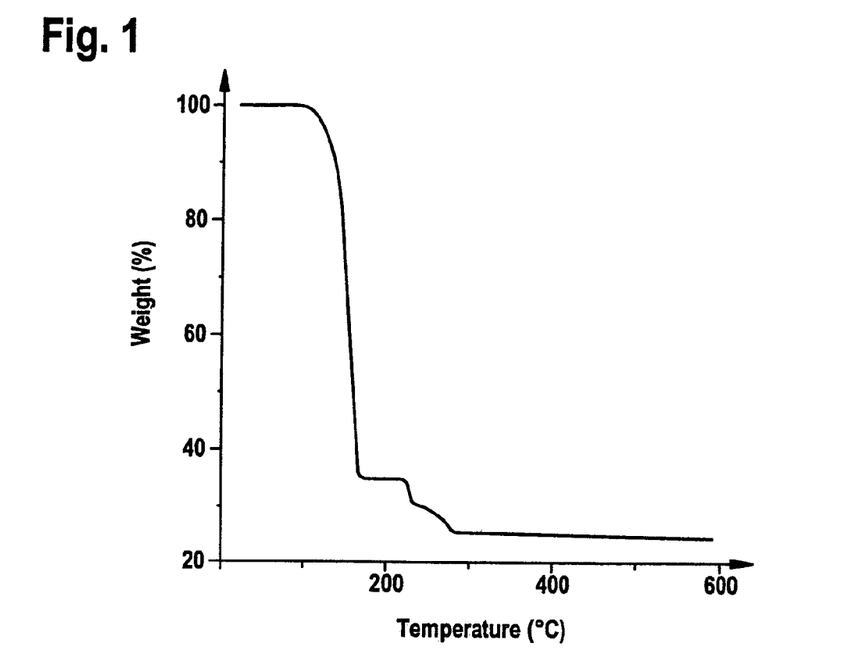
FIG. 1 shows the decomposition of the di{[bis(trimethylsilyl)acetylene]-copper(I)}oxalate prepared as a function of temperature with deposition of a thin copper layer on a substrate.

FIG. 1 shows the decomposition of the di{[bis(trimethylsilyl)acetylene]-copper(I)}oxalate prepared as a function of temperature with deposition of a thin copper layer on a substrate.

Example 2

Di{[(trimethylsilyl)(n-butyl)acetylene]copper(I)}oxalate 5 ml of $Me_3SiC \equiv C^nBu$ and 1.13 g of oxalic acid are added to a suspension of 1.8 g of $Cu_2O$ in 400 ml of methylene chloride under an inert-gas atmosphere, and the mixture is stirred at room temperature for 5 hours. In order to remove insoluble residues, the solution is passed through a frit with silica gel, and the residue is washed twice with methylene chloride on the frit. The colourless solution is evaporated, and colourless crystals of $(Me_3SiC \equiv C^nBu)_2 Cu_2O_4C_2$ are obtained at −30° C.

$C_{20}H_{36}Cu_2O_4Si_2$ (523.77 g/mol). IR (KBr) [cm$^{-1}$]: $v_{C \equiv C}$ 1986, $v_{CO2}$ 1643, 1355, 1311. $^1$H-NMR (CDCl$_3$) [ppm]: 0.29 (s, 18H, SiMe$_3$), 0.93 [t, $^3J_{HH}$=7.0 Hz, 6H, (CH$_2$)$_3$CH$_3$], 1.3–1.6 [m, 4H, (CH$_2$)$_2$CH$_2$CH$_3$], 1.5–1.8 (m, 4H, CH$_2$CH$_2$CH$_2$CH$_3$), 2.58 [t, $^3J_{HH}$=7.0 Hz, 4H, CH$_2$(CH$_2$)$_2$Ch$_3$]. $^{13}$C—(CDCl$_3$) [ppm]: 0.0 (SiMe$_3$), 13.4 [(CH$_2$)$_3$CH$_3$], 21.7 [(CH$_2$)$_2$CH$_2$CH$_3$], 22.5 (CH$_2$CH$_2$CH$_2$CH$_3$), 30.9 (≡CCH$_2$), 85.4 (≡CCH$_2$), 112.9 (SiC≡C), 171.4 (CO$_2$). MS (m/e (%)): 741 (20) [M+Cu(Me$_3$SiC≡CBu)]$^+$, 587 (20) [M+Cu]$^+$, 371 (93) [M−CuO$_4$C$_2$]$^+$, 217 (100) [M−(Me$_3$SiC≡CBu)CuO$_4$C$_2$]$^+$. TG (30–1000° C., 5° C./min) two-step decomposition, 1st step temperature range 70–150° C., weight drop 53% (2 Me$_3$SiC≡CBu), 2nd step temperature range 170–300° C., weight drop 23% (2 CO$_2$), residual content 24% (2 Cu).

Figure 2:
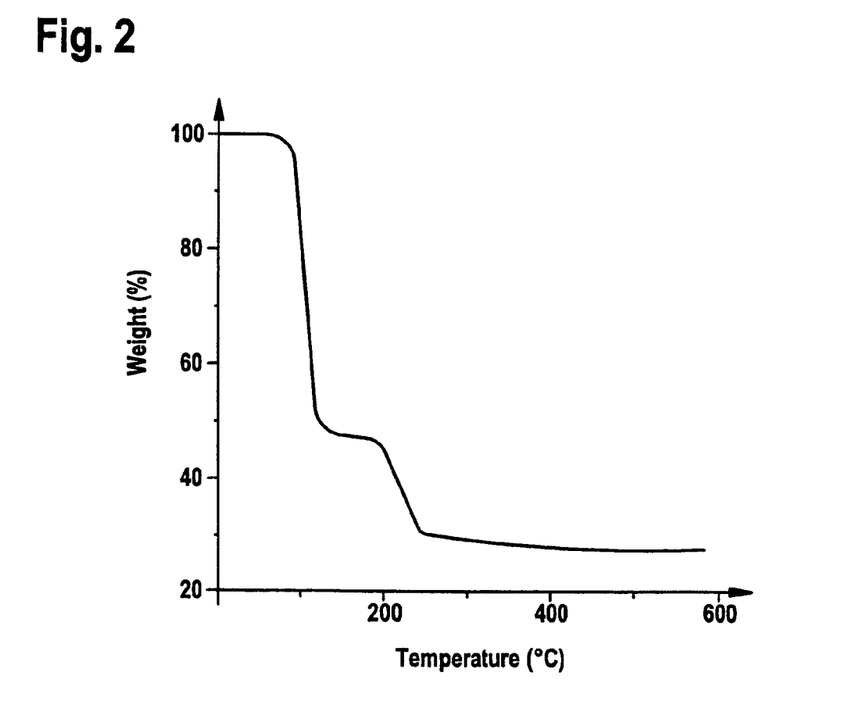
FIG. 2 shows the decomposition of the di{[(trimethylsilyl)(n-butyl)-acetylene]copper(I)}oxalate prepared as a function of temperature with deposition of a thin copper layer on a substrate.

FIG. 2 shows the decomposition of the di{[(trimethylsilyl)(n-butyl)-acetylene]copper(I)}oxalate prepared as a function of temperature with deposition of a thin copper layer on a substrate.

Example 3

Di[(vinyl-t-butyldimethylsilane)copper(I)]oxalate 4.8 ml of $H_2C \equiv CHSiMe_2{}^tBu$ and 1.13 g of oxalic acid are added to a suspension of 1.8 g of $Cu_2O$ in 400 ml of methylene chloride under an inert-gas atmosphere, and the mixture is stirred at room temperature for 5 hours. In order to remove insoluble residues, the solution is passed through a frit with silica gel, and the residue is washed twice with methylene chloride on the frit. The colourless solution is evaporated, and colourless crystals of $(H_2C \equiv CHSiMe_2{}^tBu)_2 Cu_2O_4C_2$ are obtained at −30° C.

$C_{18}H_{36}Cu_2O_4Si_2$ (499.75 g/mol). IR (KBr) [cm$^{-1}$]: $v_{CO2}$ 1647, 1344, 1312. $^1$H-NMR (CDCl$_3$) [ppm]: 0.14 (s, 12H, Si(CH$_3$)$_2$), 0.90 (s, 18H, C(CH$_3$)$_3$), 4.50 (dd, J$_{trans}$=18.3 Hz, J$_{gem}$=2.5 Hz, 2H, SiCH=CH$_2$), 4.78 (dd, J$_{trans}$=18.3 Hz, J$_{cis}$=13.3 Hz, 2H, SiCH=CH$_2$), 4.86 (dd, J$_{cis}$=13.3 Hz, J$_{gem}$=2.5 Hz, 2H, SiCH=CH$_2$). $^{13}$C-NMR (CDCl$_3$) [ppm]: −5.8 (SiMe$_2$), 16.8 (CMe$_3$), 26.2 (CMe$_3$), 91.0 (=CH$_2$), 97.4 (=CHSi), 171.6 (CO$_2$). MS (m/e (%)): 347 (62) [M−CUO$_4$C$_2$]$^+$, 206 (80) [M−(H$_2$C=CHSiMe$_2$Bu)CUO$_4$C$_2$]$^+$. TG (30–1000° C., 5° C./min) three-step decomposition, 1st step temperature range 70–130° C., weight drop 39% (H$_2$C=CHSiMe$_2{}^t$Bu, H$_2$C=CMe$_2$), 2nd step temperature range 130–170° C., weight drop 15% (H$_2$C=CHSiMe$_2$H), 3rd step temperature range 170–310° C., weight drop 19% (2 CO$_2$), residual content 27% (2 Cu).

Figure 3:
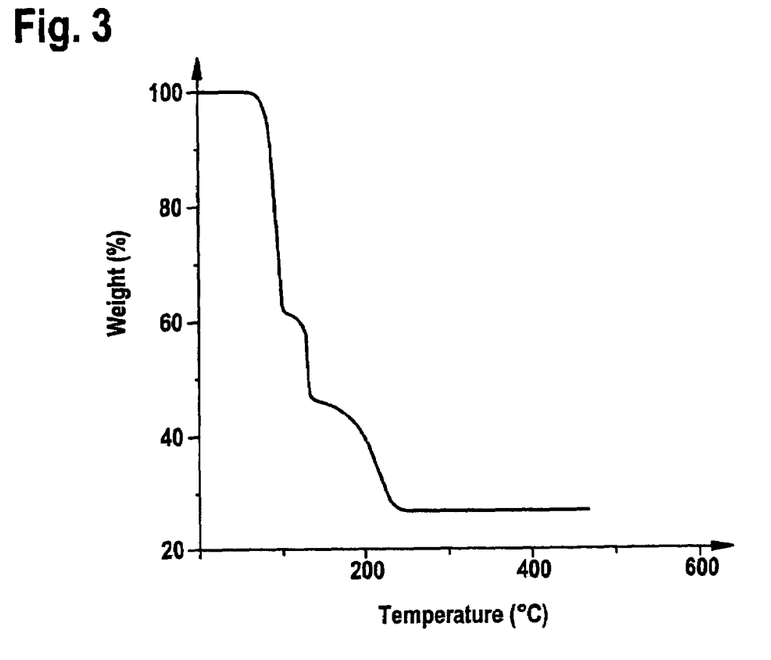
FIG. 3 shows the decomposition of the di[(vinyl-t-butyldimethylsilane)-copper(I)]oxalate prepared as a function of temperature with deposition of a thin copper layer on a substrate.

FIG. 3 shows the decomposition of the di[(vinyl-t-butyldimethylsilane)-copper(I)]oxalate prepared as a function of temperature with deposition of a thin copper layer on a substrate.

Example 4

Di[(vinyldiethylmethylsilane)copper(I)]oxalate

4.4 ml of $H_2C$=$CHSiEt_2Me$ and 1.1 g of oxalic acid are added to a suspension of 1.8 g of $Cu_2O$ in 400 ml of methylene chloride under an inert-gas atmosphere, and the mixture is stirred at room temperature for 5 hours. In order to remove insoluble residues, the solution is passed through a frit with silica gel, and the residue is washed twice with methylene chloride on the frit. The colourless solution is evaporated, and colourless crystals of $(H_2C$=$CHSiEt_2Me)_2$ $Cu_2O_4C_2$ are obtained at −30° C.

$C_{16}H_{32}Cu_2O_4Si_2$ (471.70 g/mol). IR (KBr) [cm$^{-1}$]: $\nu_{C=C}$ 1496; $\nu_{CO2}$ 1645, 1343, 1310. $^1$H-NMR (CDCl$_3$) [ppm]: 0.12 (s, 6H, SiMe), 0.65 (q, 8H, $^3J$=7.8 Hz, CH$_2$), 0.98 (t, 12H, $^3J$=7.9 Hz, CH$_3$), 4.48 (dd, J$_{trans}$=17.5 Hz, J$_{gem}$=3.6 Hz, 2H, SiCH=CHH), 4.75 (dd, J$_{trans}$=17.7 Hz, J$_{cis}$=13.0 Hz, 2H, SiCH=CH$_2$), 4.81 (dd, J$_{cis}$=13.0 Hz, J$_{gem}$=3.5 Hz, 2H, SiCH=CHH). $^{13}$C-NMR (CDCl$_3$) [ppm]: −5.5 (SiCH$_3$), 5.3 (SiCH$_2$CH$_3$), 7.3 (SiCH$_2$CH$_3$), 89.7 (H$_2$C=CH), 96.6 (H$_2$C=CH), 171.5 (COO). TG (30–1000° C., 5° C./min) two-step decomposition, 1st step temperature range 50–150° C., weight drop 50% (2H$_2$C=CHSiEt$_2$Me), 2nd step temperature range 150–320° C., weight drop 23% (2 CO$_2$), residual content 27% (2 Cu).

Figure 4:
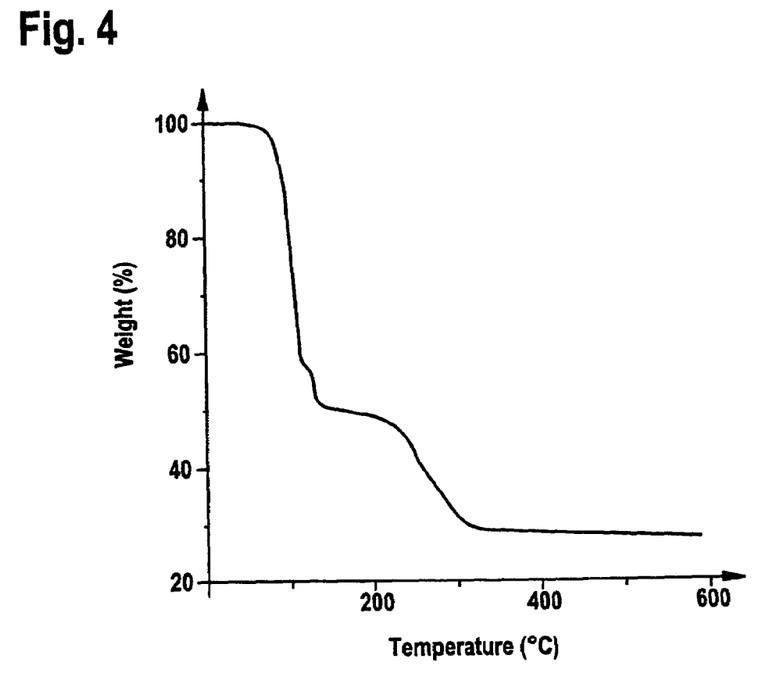
FIG. 4 shows the decomposition of the di[(vinyldiethylmethylsilane)-copper(I)]oxalate prepared as a function of temperature with deposition of a thin copper layer on a substrate.

FIG. 4 shows the decomposition of the di[(vinyldiethylmethylsilane)-copper(I)]oxalate prepared as a function of temperature with deposition of a thin copper layer on a substrate.

The invention claimed is:
1. A Compound of formula (I)

in which copper is in the oxidation state +1, and

L is R—C≡C—R' having at least one silyl or ester group,
R'HC=CHR having at least one silyl or ester group,
R'$_3$Si—C≡C—R', R'$_3$N, R'$_2$N(CH$_2$)$_n$NR'$_2$, substituted or unsubstituted 2,2'-bipyridine, 1,10-phenanthroline, P(OR')$_3$,
P(alkyl)$_3$,
R'—O—R', R'—O(CH$_2$)$_n$O—R', R'—S—R', R'—S (CH$_2$)$_n$S—R', CH$_3$—C≡N, $^t$Bu—C≡N, C$_4$H$_9$C≡N or Ph—C≡N,
where
R is A, aryl, alkylaryl or alkynyl having at least one SiR'$_3$ or COOR' group, and
R' is R, H, A, aryl, alkylaryl or alkynyl, where L, R and R' may each, independently of one another, adopt identical or different meanings in different positions of the molecule,
and
A is straight-chain or branched C1–C30-alkyl, C3–C30-cycloalkyl, straight-chain or branched C2–C30-alkenyl or straight-chain or branched C3–C30-cycloalkenyl,
aryl is C6–C10-aryl or alkylaryl,
alkylaryl is C7–C18-alkylaryl,
alkynyl is straight-chain or branched C2–C30-alkynyl.
2. A compound according to claim 1, in which
A is straight-chain or branched C1–C9-alkyl, straight-chain or branched C3–C9-cycloalkyl, straight-chain or branched C2–C9-alkenyl or
straight-chain or branched C3–C9-cycloalkenyl,
aryl is phenyl or naphthyl,
alkylaryl is tolyl or mesityl,
alkynyl is straight-chain or branched C2–C9-alkynyl,
and R and R' may each, independently of one another, adopt identical or different meanings in different positions of the molecule.
3. A compound according to claim 1, in which
A is methyl, ethyl, n- and i-propyl and n-, i-tert-butyl, cyclopropyl, cyclobutyl, cyclopentyl, cyclohexyl, vinyl, C2–C6- alkenyl, propenyl, butenyl, pentenyl, hexenyl, cyclopropenyl, cyclobutenyl, cyclopentenyl, cyclopentadienyl or methylcyclopentadienyl,
aryl is phenyl or naphthyl,
alkylaryl is tolyl or mesityl,
alkynyl is ethynyl, propynyl, butynyl, pentynyl or hexynyl,
and R and R' may each, independently of one another, adopt identical or different meanings in different positions of the molecule.
4. A compound according to claim 1, in which L is R—C≡C—R' or R'HC=CHR, each having at least one silyl or ester group, and the radicals R and R' are as defined in claim 1.
5. A compound according to claim 1, in which L is R'$_3$Si—C≡C—R', where R' is SiMe$_3$, CH$_3$, C$_2$H$_5$, C$_3$H$_7$, C$_4$H$_9$, phenyl, COOMe or COOEt.
6. A compound according to claim 1, in which L is Me$_3$SiC≡C—SiMe$_3$, Me$_3$Si—C≡C—$^n$Bu, McOOC—C≡C—COOMe, EtOOC—C≡C—COOEt or Me$_3$Si—C≡C—R', in which R' is CH$_3$, C$_2$H$_5$, C$_3$H$_7$, phenyl, COOMe or COOEt.
7. A compound according to claim 1, in which L is H$_2$C=CHSiMe$_3$, H$_2$C=CHCOOCH$_3$, H$_2$C=CHCOOC$_2$H$_5$ or H$_2$C=CHSiR'$_3$, in which R', independently of one another, is CH$_3$, C$_2$H$_5$, C$_3$H$_7$, C$_4$H$_9$, HC=CH$_2$ or phenyl.
8. A compound according to claim 1, in which L is CH$_3$—C≡N, $^t$Bu C≡N, C$_4$H$_9$C≡N, Ph—C≡N; N(CH$_3$)$_3$, N(C$_2$H$_5$)$_3$, H$_2$N (CH$_2$)$_2$¯NH$_2$, (CH$_3$)$_2$N¯(CH$_2$)$_2$—N(CH$_3$)$_2$, (C$_2$H$_5$)$_2$N¯(CH$_2$)$_2$¯N(C$_2$H$_5$)$_2$, H$_2$N—(CH$_2$)$_4$—NH$_2$, (CH$_3$)$_2$ N—(CH$_2$)$_4$—N(CH$_3$)$_2$, (C$_2$H$_5$)$_2$N—(CH$_2$)$_4$N(C$_2$H$_5$)$_2$, 2,9-dimethyl-1,10-phenanthroline; P(OCH$_3$)$_3$, P(OC$_2$H$_5$)$_3$, P(OC$_6$H$_{11}$)$_3$, P(OPh)$_3$; P(CH$_3$)$_3$, P(C$_2$H$_5$)$_3$, P(C$_3$H$_7$)$_3$, P(C$_4$H$_9$)$_3$, P(C$_6$H$_{11}$)$_3$; C$_2$H$_5$—O—C$_2$H$_5$, CH$_3$—O—C$_4$H$_9$, CH$_3$O—(CH$_2$)$_2$—OCH$_3$, C$_2$H$_5$O—(CH$_2$)$_2$—OC$_2$H$_5$, CH$_3$—S—CH$_3$, C$_2$H$_5$—S—C$_2$H$_5$, C$_3$H$_7$—S—C$_3$H$_7$, Ph—S—Ph, Ch$_3$S—(CH$_2$)$_2$—SCH$_3$, CH$_3$S—(CH$_2$)$_3$—SCH$_3$, C$_2$H$_5$S—(CH$_2$)$_2$—SC$_2$H$_5$ or PhS—(CH$_2$)$_2$—SPh.

9. A compounds of formula (I) di{[bis(trimethylsilyl)acetylene]copper(I)}oxalate, di{[(trimethylsilyl)(n-butyl)acetylene]copper(I)}oxalate, di[(vinyl-t-butyldimethylsilane)copper(I)]oxalate, di[(vinyldiethylmethylsilane)copper(I)]oxalate.

10. A process for the preparation of a compound of the general formula (I) according to claim 1, comprising reacting Cu$_2$O with oxalic acid and a Lewis base L in an inert solvent, and isolating the resultant product.

11. A process according to claim 10, wherein an inert aprotic organic solvent is used which is an open-chain or cyclic aliphatic or aromatic hydrocarbon, a halogenated aliphatic or halogenated aromatic hydrocarbon or a linear or cyclic ether or a mixture of these hydrocarbons.

12. A process according to claim 10, further comprising utilizing a solvent which is pentane, hexane, heptane, cyclohexane, toluene, methylene chloride, trichloromethane, chlorobenzene, diethyl ether or tetrahydrofuran.

13. A process according to claim 10, carried out under a protective-gas atmosphere.

14. A process according to claim 13, wherein the protective gas employed is nitrogen or argon.

15. A process according to claim 10, wherein the Lewis base L is employed in at least twice the stoichiometric ratio of the starting materials Cu$_2$O and oxalic acid.

16. A process according to claim 10, wherein the starting materials Cu$_2$O, oxalic acid and Lewis base L are employed in a stoichiometric ratio of from 1:1:2 to 1:1:4.

17. A process according to claim 10, wherein two different Lewis bases L are employed in identical molar amounts.

18. A process according to claim 10, wherein the reaction is carried out within a reaction time of from about 1 to 24 hours at a temperature in the range from about −30 to +100° C.

19. A process according to claim 10, carried out at room temperature.

20. A process according to claim 10, wherein, when the reaction is complete, insoluble constituents are separated off, and the reaction product is isolated from the solution and, if necessary, purified, or in that the reaction product is separated from the reaction mixture by extraction, isolated and, if necessary, purified.

21. A process according to claim 10, wherein insoluble constituents are separated off by filtration.

22. A process for the production of highly pure, thin metallic copper layers, wherein compounds of metallic copper layers, wherein compounds of formula (I) according to claim 1 are heated, causing elimination of the Lewis base L and deposition of metallic copper deposited through decarboxylation.

23. A process according to claim 22, wherein the elimination of the Lewis base L is carried out at a temperature in the range from about 50 to about 200° C., and the decarboxylation is completed at a temperature in the range from about 150 to 350° C. with formation of metallic copper.

24. A process according to claim 22, wherein the Lewis base L eliminated is recycled and, re-employed in a process for preparing compounds of general formula (I) by reacting Cu$_2$O with oxalic acid and the Lewis base in an inert solvent and isolating the product, and then the resultant compounds of formula (I) are used for the production of highly pure, thin metallic copper layers.

* * * * *

UNITED STATES PATENT AND TRADEMARK OFFICE
CERTIFICATE OF CORRECTION

PATENT NO. : 7,169,947 B2 Page 1 of 1
APPLICATION NO. : 10/519163
DATED : January 30, 2007
INVENTOR(S) : Katrin Koehler It is certified that error appears in the above-identified patent and that said Letters Patent is hereby corrected as shown below:

Column 13, line 9 reads "compounds", should read -- compound --

Signed and Sealed this

First Day of April, 2008

JON W. DUDAS
*Director of the United States Patent and Trademark Office*